(12) United States Patent
Weber

(10) Patent No.: US 8,282,650 B2
(45) Date of Patent: Oct. 9, 2012

(54) SURGICAL INSTRUMENT TO MEASURE AN INTERVERTEBRAL SPACE

(76) Inventor: Helmut Weber, Emmingen-Liptingen (DE)

( * ) Notice: Subject to any disclaimer, the term of this patent is extended or adjusted under 35 U.S.C. 154(b) by 566 days.

(21) Appl. No.: 12/427,394

(22) Filed: Apr. 21, 2009

(65) Prior Publication Data

US 2010/0114106 A1 May 6, 2010

(30) Foreign Application Priority Data

Apr. 21, 2008 (EP) .................... 08007694

(51) Int. Cl.
*A61B 17/58* (2006.01)
*A61B 17/60* (2006.01)
*A61F 2/00* (2006.01)

(52) U.S. Cl. ........................ 606/102; 606/105

(58) Field of Classification Search .............. 606/90, 606/102, 99, 105; 600/214
See application file for complete search history.

(56) References Cited

U.S. PATENT DOCUMENTS

| | | | |
|---|---|---|---|
| 6,190,414 B1 * | 2/2001 | Young et al. | 623/17.15 |
| 2005/0113842 A1 * | 5/2005 | Bertagnoli et al. | 606/90 |
| 2006/0069436 A1 * | 3/2006 | Sutton et al. | 623/17.13 |
| 2006/0074431 A1 | 4/2006 | Sutton et al. | |
| 2007/0209222 A1 * | 9/2007 | Fischer et al. | 33/512 |
| 2007/0260260 A1 | 11/2007 | Hahn et al. | |

FOREIGN PATENT DOCUMENTS

| | | |
|---|---|---|
| EP | 2 111 824 | 4/2010 |
| WO | WO 03/037230 | 5/2003 |
| WO | WO 2005/006944 | 1/2005 |
| WO | WO 2006/027098 | 3/2006 |

OTHER PUBLICATIONS

EP Serial No. EP 08007694.6-2310 filed Apr. 21, 2008, German EP Search Report (6 pages).

* cited by examiner

*Primary Examiner* — Kevin T Truong
*Assistant Examiner* — Olivia C Chang
(74) *Attorney, Agent, or Firm* — Andrew F. Young, Esq.; Lackenbach Siegel, LLP

(57) ABSTRACT

The invention is a surgical instrument for measuring an intervertebral space. On the distal end of a handle of the instrument there are at least two measurement plates, whereby an interval between the measurement plates, and an angle enclosed by the measurement plates, are adjustable.

18 Claims, 5 Drawing Sheets

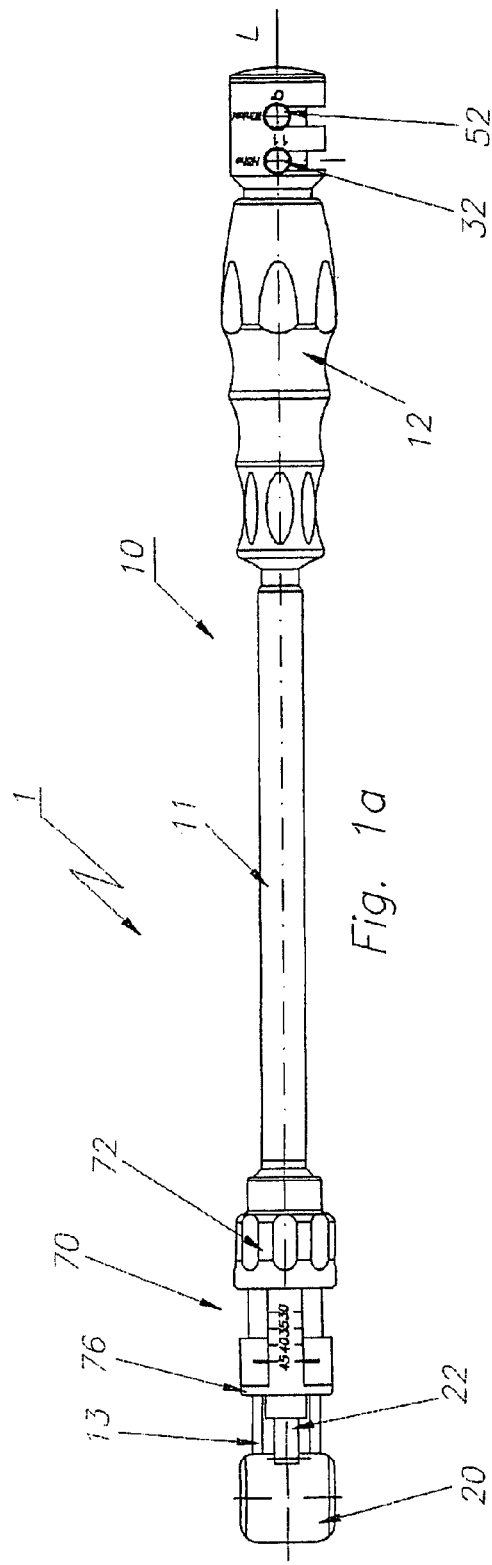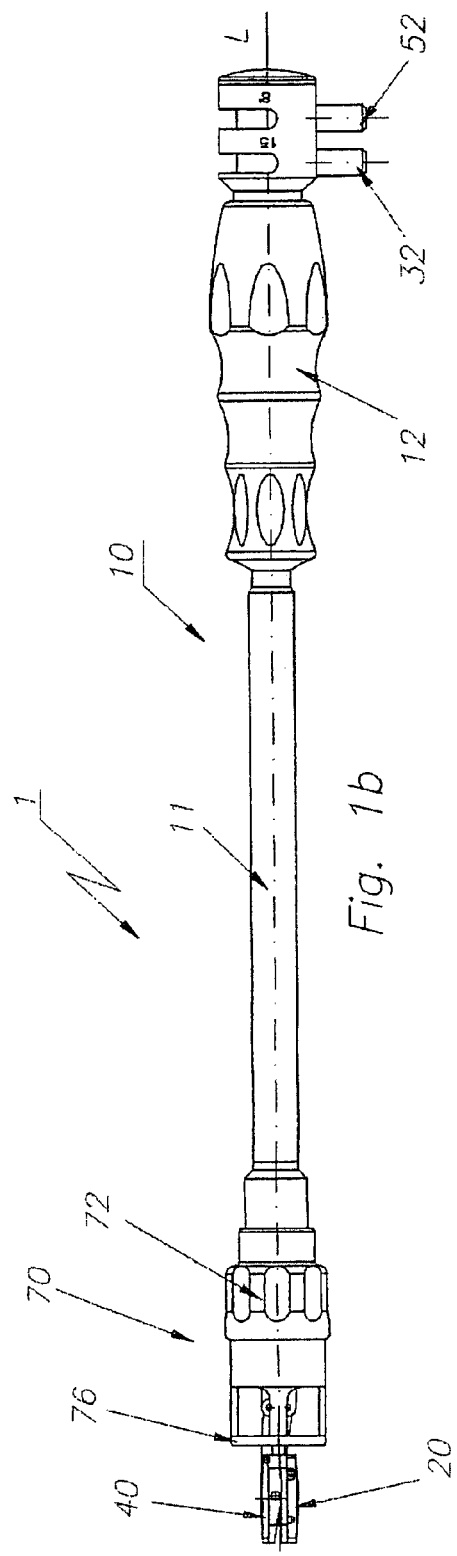

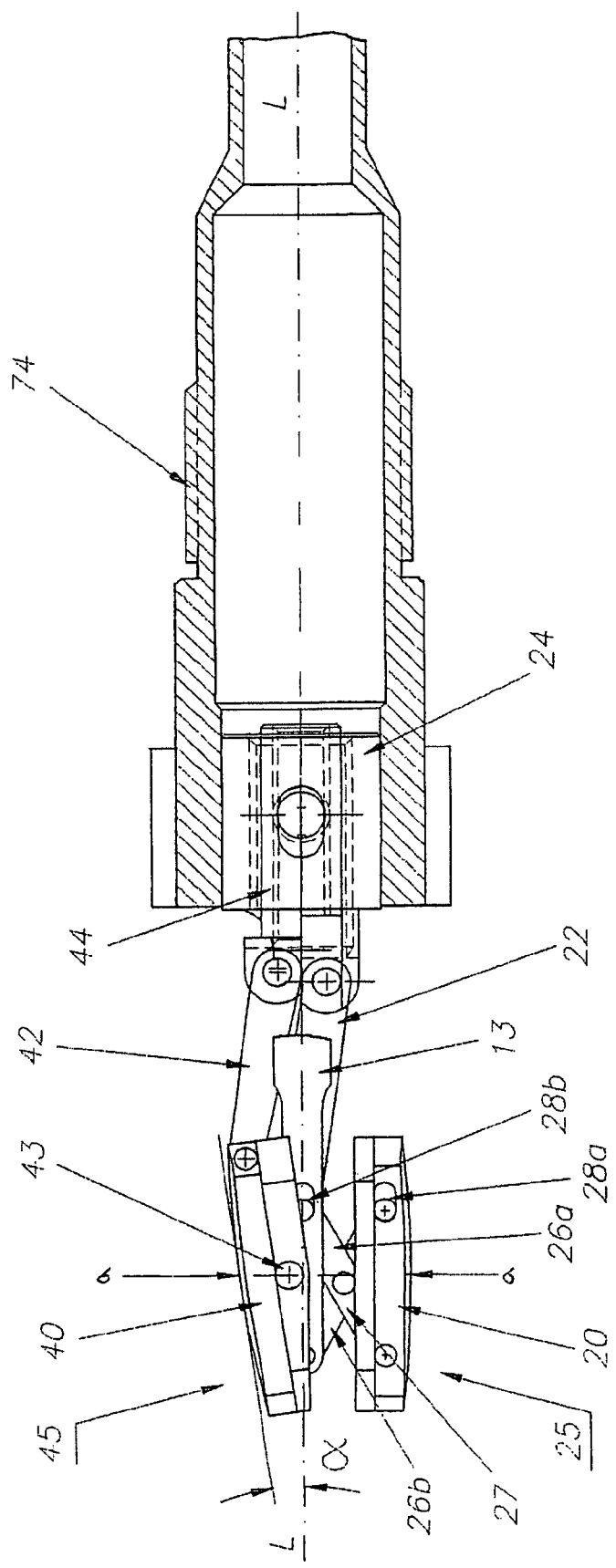

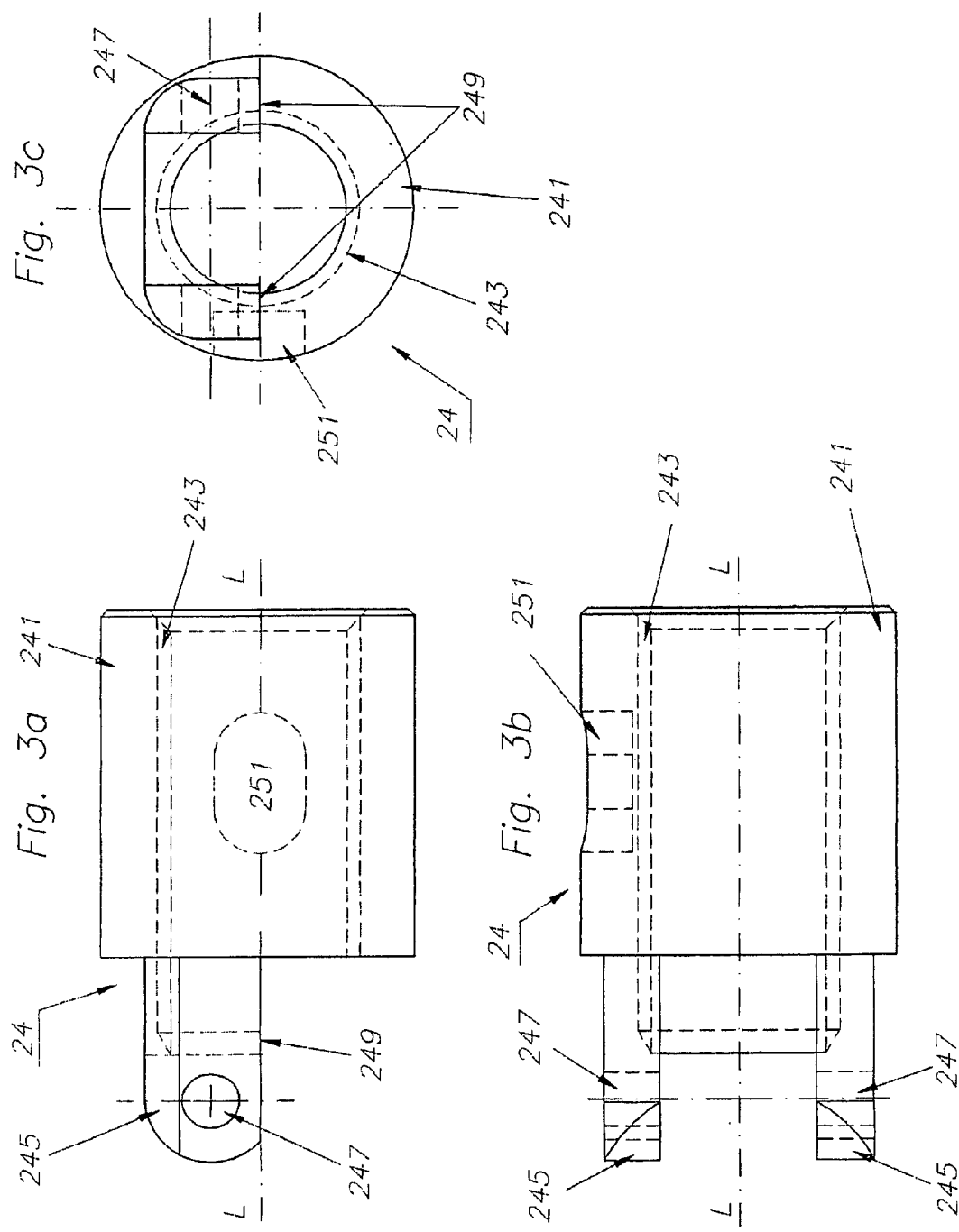

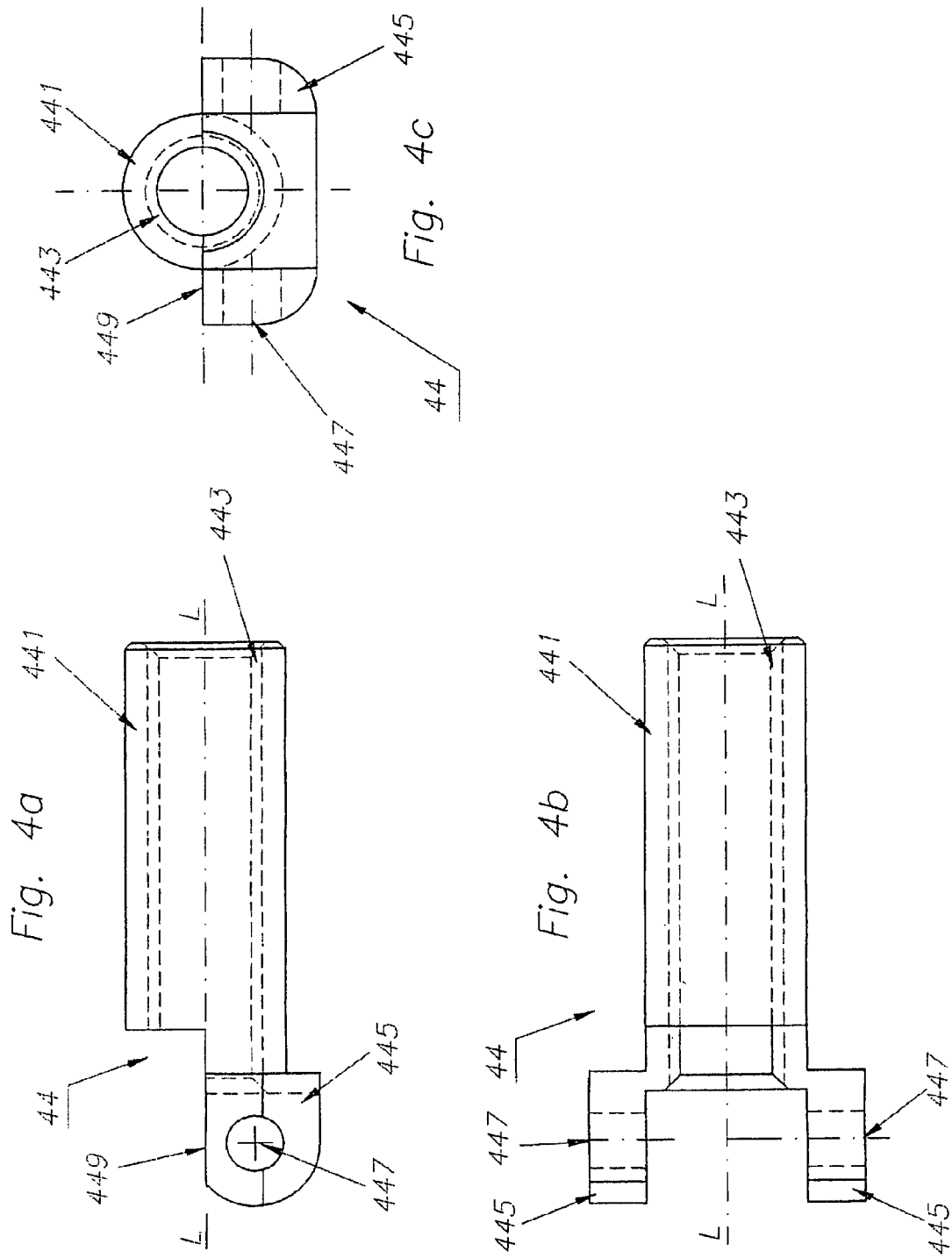

SURGICAL INSTRUMENT TO MEASURE AN INTERVERTEBRAL SPACE

CROSS REFERENCE TO RELATED APPLICATIONS

This application claims priority from European Patent Application No. 08 007 694.6, filed Apr. 21, 2008, the entire contents of which are herein incorporated fully by reference.

FIGURE FOR PUBLICATION

FIG. 2.

BACKGROUND OF THE INVENTION

1. Field of the Invention

The present invention relates to a medical device for measuring spatial relationships between anatomical structures. More specifically, the present invention relates to a surgical instrument for measuring an intervertebral space in a precise manner so as to allow for optimal restoration of a damaged area.

2. Description of the Related Art

In prosthetics for intervertebral disks, it is customary to use so-called intervertebral prostheses as disk replacements. Such intervertebral prostheses are inserted between the vertebral bodies as part of an operation, replacing the defective disks removed earlier. To ensure that the original mobility and function of the spinal column is optimally restored, it is necessary that the damaged intervertebral space be reconstructed with optimal precision, and that the dimensions and positioning of an intervertebral prosthesis be chosen in optimal fashion. As a rule, intervertebral prostheses of the type mentioned consist of two prosthetic plates, each connected with a vertebral body. In some versions, between the prosthetic plates, a prosthesis core is placed, on which the prosthesis plates glide and assume the damping function of the removed disk. In determining the dimensions for an intervertebral prosthesis to be inserted, especially the area of the prosthetic plates, the overall height of the intervertebral prosthesis and an angular setting of the surfaces of the prosthetic plates facing the vertebral bodies to each other are decisive.

The related arts teach that the measurements of the intervertebral prosthesis are taken preoperatively using X ray or CAT imagery, and during the operation are verified after removal of the disk by test use of implants. Implant measurements are verified by inserting a test implant between the vertebral bodies mechanically spread apart from each other; the spreading is released; and then, using an X ray image, the register form of the implant is checked.

What is not appreciated by the prior art is that it is necessary to spread the vertebral bodies multiple times to remove and re-insert the test prostheses for insertion and checking of the intervertebral prostheses. On the one hand, this takes up a large part of the time for surgery; and, on the other hand, it necessitates unnecessary mechanical loads on the patient's spinal column.

Accordingly, the inventors recognize a need for an improved surgical instrument for measuring an intervertebral space in a precise manner so as to allow for optimal restoration of a damaged area

ASPECTS AND SUMMARY OF THE INVENTION

An aspect of the present invention is to make available a surgical instrument to measure an intervertebral space, by which it is possible to determine the dimensions for an intervertebral prosthesis to be inserted more quickly and more simply, and in a manner that is easier on the patient.

The present invention relates to a surgical instrument for measuring an intervertebral space. On the distal end of a handle of the instrument there are at least two measurement plates, whereby an interval between the measurement plates, and an angle enclosed by the measurement plates, are adjustable.

According to an embodiment of the present invention there is provided a surgical instrument for measuring an intervertebral space. The surgical instrument comprises a handle having a distal end. At the distal end there are provided at least two measurements plates, shown without limitation as a first and a second measurement plate. There is an interval between the first and the second measurement plates wherein the interval is adjustable. Also defined, is an adjustable angle (discussed below as $\alpha$, but not limited thereto) enclosed by the first measurement plate and the second measurement plate.

The advantage of the present invention is that owing to both the interval and enclosed angle being adjustable, only one spreading procedure is necessary to insert the surgical instrument; with it, due to the adjustability of the interval and the angle enclosed by the measurement plates, an in situ variation of the size is possible, so that through a one-time insertion of the surgical instrument, the exact fit of various implant dimensions can be checked and then immediately an intervertebral prosthesis with the correct dimensions can be inserted.

It is advantageous if, simultaneous with the implant dimensions, it is also possible to determine the depth at which the implant is placed, proceeding from the anterior side of the vertebral body via a movable deep stop. Such a deep stop can, for example, be determined by means of a cover surrounding the handle, which can for example be implemented by a cylindrical cover that can be screwed via an outer thread. The advantage of a cylindrical cover that surrounds the entire handle, is that only a single stop is present, and thus with a single adjustment the stop can be determined simultaneously for the two vertebral bodies between which the intervertebral prosthesis is to be mounted.

For a mechanical implementation of the surgical instrument, it is advantageous if a first measurement plate is configured for adjusting the distance and a second measurement plate is configured for setting the angle enclosed between the measurement plates. The mechanical implementation in this case is unique, so that for the one plate, all that must be provided is a mechanism for height adjustment; and, for the other plate, a mechanism to adjust the plate angle.

A height adjustment can be effected for example with a spreader that can be configured like an accordion lift table. With this it is advantageous that such a spreader execute a parallel adjustment of the measurement plate without any additional tipping.

Preferably, such a spreader has two scissors-like members able to move relative to each other, of which one can be controlled using a coupling rod, whereby the other is pivoted by means of an axle.

Linear motion of the coupling rod can be generated with especial ease from a threaded rod's rotational motion via a threaded bushing, which is placed in the handle so as not to turn. Owing to such guidance it is possible with particular ease to precisely adjust small motion steps of the one scissors-like part via a thread with a small passage height. This can be done, for example, using a threaded rod that is placed in the handle. On a proximal end of such a threaded rod, then, for example, an operating lever or an appropriately configured rotary knob can be placed. The advantage of using a threaded rod to operate it is that through selection of the threading, a reduction can be attained simply for the adjustment path.

For adjusting the angle enclosed by the measurement plate, it is advantageous to provide a revolving mechanism. Such a revolving mechanism can be formed with particular ease by supporting the second measurement plate along an axis perpendicular to the longitudinal axis of the handle and parallel to the first measurement plate. It is especially advantageous if this axis is provided in a central area of the second measurement plate, so that owing to a swiveling of the second measurement plate, the centrally determined interval of the measurement plates does not change.

It is possible, with relative ease, to generate a swiveling motion of the second measurement plate from a linear motion using a connecting rod. Such a connecting rod converts a linear motion, for example that of a second threaded bushing, into a rotary motion, thus allowing the swivel motion of the second measurement plate.

The linear motion of the second threaded bushing, in turn, is easily to adjustable via a second threaded rod that also can be situated in the handle. An especially elegant solution is produced when the handle is shaped as a tube and the second threaded rod is placed in the first threaded rod, which is likewise configured as a tube. This solution is also particularly elegant for the threaded bushing. In this case, the second threaded bushing is placed concentric to the first threaded bushing and is placed so as to slide in it.

The overall surgical instrument is advantageously manufactured from biocompatible and sterilizable material such as stainless steel or titanium. The handle can, for example, be sprayed with a silicon rubber, to ensure better handling qualities.

The above, and other aspects, features and advantages of the present invention, will become apparent from the following description read in conjunction with the accompanying drawings, in which like reference numerals designate the same elements.

BRIEF DESCRIPTION OF THE DRAWINGS

FIG. 1a is top view of an invention-specific surgical instrument.
FIG. 1b is a side view of surgical instrument from FIG. 1a.
FIG. 2 is a partial lateral cross-section view of the distal end of the surgical instrument from FIG. 1b.
FIG. 3a is a side view of a first threaded bushing as utilized in the present invention.
FIG. 3b is a top view of the threaded bushing from FIGS. 3a and 3b.
FIG. 3c is a front view of the threaded bushing from FIGS. 3a and 3b.
FIG. 4a is a side view of a second threaded bushing of the present invention.
FIG. 4b is a top view of the threaded bushing from FIG. 4a.
FIG. 4c is a front view of the threaded bushing from FIGS. 4a and 4b.

DETAILED DESCRIPTION OF THE PREFERRED EMBODIMENTS

Figure 5:
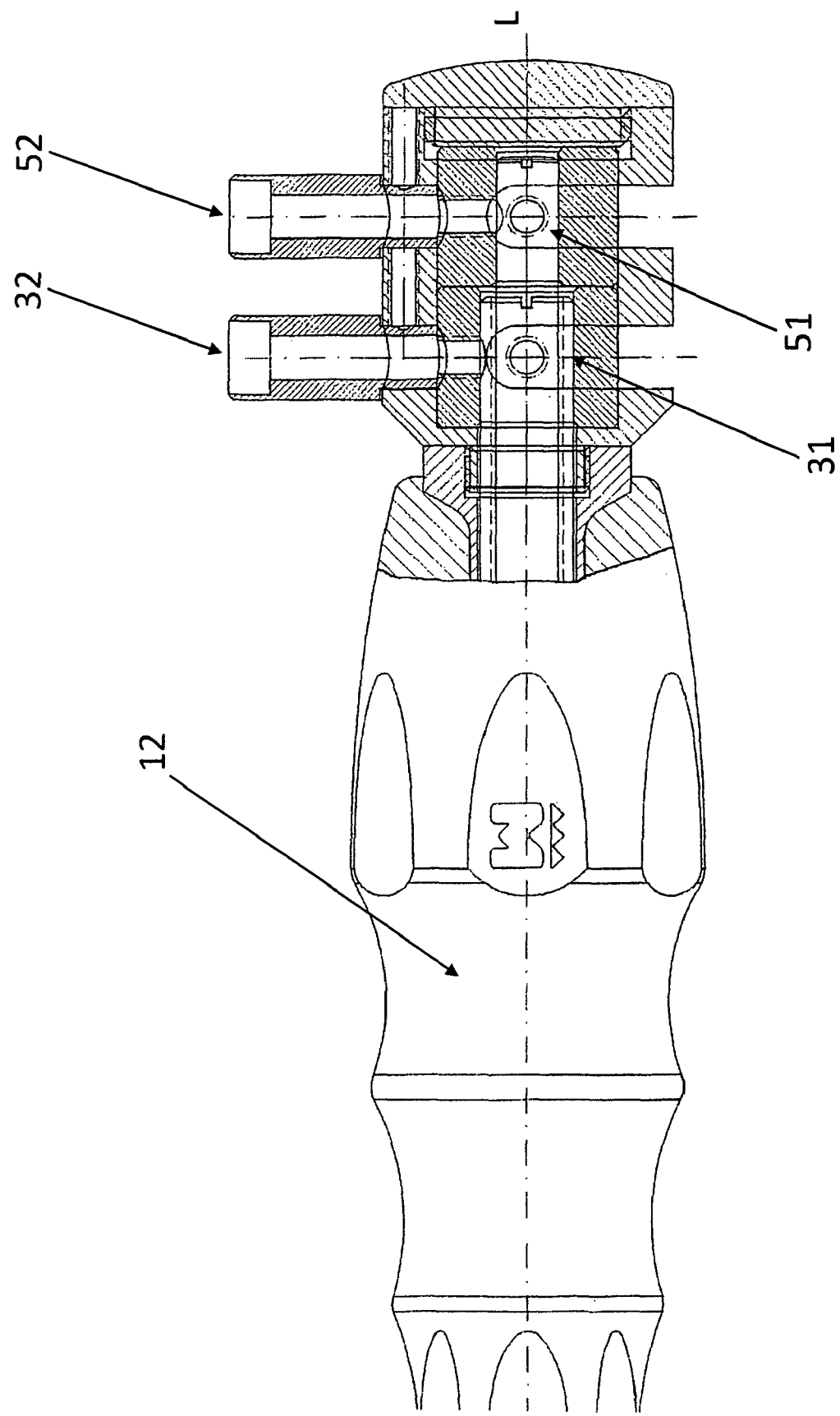
FIG. 5 is a partial lateral cross-section view of the handle grip of the present invention wherein the first and second threaded rods are depicted.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, and below may be used with respect to the drawings. These and similar directional terms should not be construed to limit the scope of the invention in any manner. The words "connect," "couple," and similar terms with their inflectional morphemes do not necessarily denote direct and immediate connections, but also include connections through mediate elements or devices.

FIG. 1a shows a top view of an invention-specific surgical instrument 1 for measuring an intervertebral space. The surgical instrument 1 has a handle 10 that consists of a handle grip 12 as well as a shaft 11 placed on handle grip 12. At the distal end of handle 10 a plate holder 13 is situated, on which two measurement plates 20, 40 (plate 40 shown in FIGS. 1b, 2) are arrayed. At the distal end of handle 10, behind measurement plates 20, 40, a movable and adjustable depth stop 70 is additionally placed, which in essence exhibits a turnable casing 72 that sits on an outer thread 74 of handle 10, as well as a stop 76 connected with the casing 76. In the distal area, a deep stop 76 completely surrounds surgical instrument 1, so that by means of the stop 76, it is simultaneously adjustable for one vertebral body found above and one below the measurement plates 20, 40.

At the proximal end of handle 10, behind handle grip 12, there is an operating device with a first operating lever 32 and a second operating lever 52. The operating levers 32, 52 act via respective rotating threaded rods 31, 51 (as are more clearly shown in FIG. 5) placed in handle 10 on the adjustment mechanism placed in the distal area for measurement plates 20, 40.

FIG. 1b depicts the surgical instrument from FIG. 1a in a side view. In this side view, on the proximal end of handle 10, the operating levers 32, 52 are especially easy to perceive, are placed radially on threaded rods 31, 51 (as are more clearly shown in FIG. 5) in handle 10.

At the distal end of handle 10, the depth stop 70 is turned until it reaches a distal end position, i.e., so that stop 76 lies immediately behind measurement plates 20, 40; while in FIG. 1a, it is in a proximal end position right at the transition of handle 10 to plate holder 13.

FIG. 2 shows the adjustment mechanism of the distally placed measurement plates 20, 40 from FIGS. 1a and 1b in an enlarged cross-sectional depiction. For better visibility, the depth stop 70 is not shown in this depiction.

In the sectional depiction of FIG. 2, in the right section of the drawing, the distal area of handle 10 is shown, to which plate holder 13 is attached. On plate holder 13, via scissors-like mechanism 27, which is movable according to the principle of an accordion-fold lift table, there is placed a first measurement plate 20, whose interval relative to plate holder 13 and second measurement plate 40 is adjustable. Additionally, placed on plate holder 13, placed over an axle 43, is the second measurement plate 40, which is situated at minimum in a position parallel to the first measurement plate 20. Further, the inclination angle α of second measurement plate 40 is adjustable relative to first measurement plate 20 via a connecting rod 42.

The scissors-like mechanism 27 of first measurement plate 20 is subject to linear control via a coupling rod 22, (i.e., linear motion of threaded bushing 24 is transmitted via a coupling rod 22 to a first scissors piece 26a of scissors-like mechanism 27). The scissors pieces 26a, 26b of scissors-like mechanism 27 are connected movably and turnably relative to each other. A first end of first scissors piece 26a is pivoted in a first longitudinal hole 28a in plate holder 13 and so as to slide along longitudinal axis L. A second end of first scissors piece 26a is placed over an axle in first measurement plate 20. A first end of the second scissors piece 26b is placed over an axle in plate holder 13, while a second end of second scissors piece 26b is able to turn in a second longitudinal hole 28b, and to slide parallel to longitudinal axis L in first measurement plate 20. Coupling rod 22 acts on the first end of first scissors piece 26a placed in first longitudinal hole 28a of plate holder 13. Owing to a displacement of first scissors piece 26a along handle 10's longitudinal axis L, the interval of first measurement plate 20 to plate holder 13 is changed according to the accordion lift table principle, thus altering the interval "a" (see FIG. 2) of measurement plates 20, 40, that is defined relative to the first measurement plate 20 at the location of axis 43.

The second measurement plate 40 is placed over a centrally placed axle 43 on plate holder 13. A linear motion of second threaded bushing 44 is transferable into a tipping motion of second measurement plate 40 about axle 43 via a connecting rod 42 that engages on the proximal end of second measurement plate 40. Support is provided for second measurement plate 40 in such a way that the interval is not changed by a tipping motion of second measurement plate 40 in a central area of measurement plate 20.

The coupling rod 22 and connecting rod 42 are controlled by threaded bushings 24, 44 placed in the handle 10. The first threaded rod 24 is placed so as not to turn in handle 10 and configured as casing 241, in which the second threaded bushing 44 sits. The first threaded bushing 24 is controlled via a first tube-shaped threaded rod 31 (not shown here, shown later in FIG. 5) and converts a turning motion of the first threaded rod 31 (not shown) into a linear motion along longitudinal axis L of first threaded bushing 24, so that by turning the first threaded rod 31 (as is shown in FIG. 5), the height of first measurement plate 20 is controllably adjustable. In the first tube-shaped threaded rod 31 there is placed a second threaded rod 51 (as is also shown in FIG. 5), which second threaded bushing 44 controls. Second threaded bushing 44 is placed so as not to turn via a contact surface 449 in first threaded bushing 25.

FIGS. 3a to 3c show various views of first threaded bushing 24, as it is used in FIG. 2 to control first measurement plate 20.

FIG. 3a is a side view of first threaded bushing 24, in which the structure of first threaded bushing 24 is easily perceived. First threaded bushing 24 essentially consists of a casing 241, in which an inner thread 243 is placed. On the front side of casing 241 is a fork-shaped projection 245 with a borehole 247 in each of the anus, whereby the connection to coupling rod 22 can be made via borehole 247. An outer thread of the first threaded rod (not shown) engages the inner thread 243. The first threaded bushing 24 is supported by a bolt which engages into a longitudinal hole 251 situated on the circumference of casing 241, and sits so as not to turn in a corresponding recess of handle 10, so that rotation of first threaded rod 51 (as is shown more clearly in FIG. 5) due to engagement of threading evokes a linear motion of first threaded bushing 24.

In FIG. 3b, the forklike extension 245 is easily recognized. The forklike extension 245 extends outside the thread diameter of bushing 241, and through its fork-shaped design and the boreholes 247, it offers a possibility to attach coupling rod 22 through an axis placement with an axis transverse to longitudinal axis L on threaded bushing 24.

In the front view of FIG. 3c, it is easy to perceive that projection 245 extends only in one half of the cylindrically formed threaded bushing 24, and forms a contact surface 249 turned toward the central axis. In an assembled state, contact surface 249 stands in contact with a contact surface 449 of second threaded bushing 44, and thus ensures they are positioned so as not to turn.

In FIGS. 4a to 4c, various views are shown of second threaded bushing 44 as it is used according to FIG. 2 for controlling the revolving mechanism 45.

FIG. 4a shows a side view of second threaded housing 44. In this view, the design of second threaded housing 44 is perceived with particular ease. The second threaded bushing 44 essentially consists of a casing 441, into which an inner thread 443 is placed. On the front side, proceeding from the casing 441, extends a fork-shaped extension 445, in which a borehole 447 is situated. The connection to the connecting rod 42 can be created via borehole 447. As with the first threaded bushing 24, the projection 445 is configured to be only half the radius of casing 441, and forms a contact surface 449 there, which in an assembled state adjoins contact surface 249 of first threaded bushing 24. Through the form-locked arrangement of these contact surfaces 249, 449 is ensured a support of second threaded bushing 44 in first threaded bushing 24 so as not to turn.

FIG. 4b shows a top view of second threaded bushing 44. In this top view, the fork-shaped projection 445 with a borehole 447 made in both legs of projection 445 is easily perceived. Through the boreholes 447, in an assembled state, an axle in turn is run transverse to longitudinal axis L, by means of which the connecting rod 42 is supported, so that linear motion of threaded bushing 44 can be transmitted via connecting rod 42 to second measurement plate 40.

FIG. 4c shows a front view of second threaded bushing 44, in which the contact surface 449 formed by continuation 445 is especially well perceived.

The two measurement plates 20, 40 are operated according to the design presented above through a rotational manipulation of one of the two (or both) operating levers 32, 52 about handle 10's longitudinal axis L. Manipulation of the first operating lever 32, causes the tube-shaped first threaded rod 31 (as is more clearly shown in FIG. 5) to turn, which results in a translational motion of first threaded bushing 24 on the distal end of handle 10. Due to the translational motion of first threaded bushing 24, via coupling rod 22, one of the scissors pieces 26 is moved so that with the scissors-like mechanism 27, the interval "a" (as shown with the arrows) between measurement plates 20, 40 is changed. Manipulation of second operating lever 52 causes a rotational motion of the second threaded rod 51 which is placed in the first threaded rod 31. This rotational motion causes a translational motion of second threaded bushing 44, which in turn, via connecting rod 42, induces a tipping motion of second measurement plate 40 about axle 43. In this way, the angle α enclosed by measurement plates 20, 40 is adjustable.

Thus, during the surgical operation, after the spreading and removal of the disk, measurement plates 20, 40 of surgical instrument 1 are brought into the intervertebral space, whereby a first basic adjustment is made according to values determined through X-raying or computer-aided tomography. Then, in a further X-ray image, the exact fit of measurement plates 20, 40 of surgical instrument 1 (also thus the exact fit of a prosthesis prepared using the corresponding values), is checked. In case the desired exact fit is not attained, with the invention-specific surgical instrument 1 it is possible to undertake an adaptation of measurement and carry out another check of the exact fit in yet another x-ray image. No necessity exists to spread the spinal column to remove and again insert a test implant. In this way, it is now recognized that a substantial savings in time and cost is attained and, in particular, this makes possible an operation that is easier on the patient.

Turning next to FIG. 5, there is shown a partial cross-sectional view of the previously described handle grip 12 of the present invention wherein the first and second threaded rods 31, 51 are more clearly depicted. At the proximal end of handle 10 (see FIGS. 1a and 1b), behind handle grip 12, there is shown an operating device with first operating lever 32 and a second operating lever 52. The operating levers 32, 52 act rotationally via threaded rods 31, 51 (as shown) placed in handle 10 on the adjustment mechanism placed in the distal area for measurement plates 20, 40 (see FIG. 1b). The operating levers 32, 52 are placed radially on threaded rods 31, 51 and perpendicular to longitudinal axis "L" and rotate in movement, translating the rotational movement down rods 31, 51 to threads in respective bushings 24, 44 to provide motion relative to the contact surfaces 249, 449 and related coupling/connecting rods 22, 42.

In the claims, means or step-plus-function clauses are intended to cover the structures described or suggested herein as performing the recited function and not only structural equivalents but also equivalent structures. Thus, for example, although a nail, a screw, and a bolt may not be structural equivalents in that a nail relies on friction between a wooden part and a cylindrical surface, a screw's helical surface positively engages the wooden part, and a bolt's head and nut compress opposite sides of a wooden part, in the environment of fastening wooden parts, a nail, a screw, and a bolt may be readily understood by those skilled in the art as equivalent structures.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

What is claimed is:

1. A surgical instrument for measuring an intervertebral space, said surgical instrument comprising:
    (a) a handle having a distal end and a depth stop that is movable along the longitudinal axis of said handle;
    (b) a first measurement plate on said distal end;
    (c) a second measurement plate on said distal end;
    (d) a spreading device for adjustment of an interval between said first measurement plate and said second measurement plate, wherein a first threaded bushing is provided on a coupling rod to generate a linear motion of said coupling rod from a rotational motion of a first threaded rod to actuate said spreading device, said coupling rod, said first threaded bushing, and said first threaded rod being coaxially configured; and
    (e) a rotating device for adjusting an angle ($\alpha$) enclosed by said first measurement plate and said second measurement plate.

2. A surgical instrument according to claim 1, wherein said surgical instrument is manufactured of a biocompatible material.

3. A surgical instrument according to claim 2, wherein said biocompatible material is selected from the group consisting of stainless steel and titanium.

4. A surgical instrument according to claim 1, wherein said first measurement plate is configured to adjust said interval and said second measurement plate is configured to adjust said enclosed angle ($\alpha$).

5. A surgical instrument according to claim 1, wherein said rotating device is formed by pivoting said second measurement plate along an axle situated perpendicular to the longitudinal axis of said handle and parallel to said first measurement plate.

6. A surgical instrument for measuring an intervertebral space, said surgical instrument comprising:
    (a) a handle having a distal end;
    (b) a first measurement plate on said distal end;
    (c) a second measurement plate on said distal end;
    (d) an adjustable interval between said first measurement plate and said second measurement plate wherein said interval is adjustable by a spreading device comprising a first scissors piece and a second scissors piece;
    (e) an adjustable angle ($\alpha$) enclosed by said first measurement plate and said second measurement plate wherein said angle ($\alpha$) is adjustable by a rotating device, wherein said rotating device is formed by pivoting said second measurement plate along an axle situated perpendicular to the longitudinal axis of said handle and parallel to said first measurement plate; and
    (f) a connecting rod configured to generate a rotating motion of said second measurement plate from a linear motion, wherein a threaded bushing is provided to generate said linear motion of said connecting rod from a rotational motion of a threaded rod which is placed in said handle.

7. A surgical instrument according to claim 6, wherein said first measurement plate is configured to adjust said interval and said second measurement plate is configured to adjust said enclosed angle ($\alpha$).

8. A surgical instrument according to claim 7, wherein said biocompatible material is selected from the group consisting of stainless steel and titanium.

9. A surgical instrument according to claim 6, wherein said surgical instrument is manufactured of a biocompatible material.

10. A surgical instrument according to claim 6, wherein said rotating device is formed by pivoting said second measurement plate along an axle situated perpendicular to the longitudinal axis of said handle and parallel to said first measurement plate.

11. A surgical instrument according to claim 6, wherein a depth stop is provided on the distal end of said handle, said depth stop being movable along the longitudinal axis of said handle.

12. A surgical instrument for measuring an intervertebral space, said surgical instrument comprising:
    (a) a handle having a distal end opposite a proximal end;
    (b) a first measurement plate on said distal end;
    (c) a second measurement plate on said distal end;
    (d) an interval between said first measurement plate and said second measurement plate wherein said interval is adjustable;
    (e) an angle ($\alpha$) enclosed by said first measurement plate and said second measurement plate wherein said angle ($\alpha$) is adjustable by a rotating device;
    (f) a spreading device comprising a first scissors piece and a second scissors piece for adjustment of said interval, wherein said spreading device is configured according to the principle of an accordion lift table, wherein said first scissors piece and said second scissors piece can be moved relative to each other;

(g) a coupling rod configured to actuate said first scissors piece, wherein a first threaded bushing is provided to generate a linear motion of said coupling rod from a rotational motion of a first threaded rod which is placed in said handle; and (h) a connecting rod configured to generate a rotating motion of said second measurement plate from a linear motion, wherein a second threaded bushing is provided to generate said linear motion of said connecting rod from a rotational motion of a second threaded rod which is placed in said handle, and wherein said second threaded bushing is placed concentric to said first threaded bushing such that said second threaded bushing is allowed to glide with respect to said first threaded bushing.

13. A surgical instrument according to claim 12, wherein on the distal end of said handle, a depth stop is provided that is movable along the longitudinal axis of said handle.

14. A surgical instrument according to claim 12, wherein said first measurement plate is configured to adjust said interval and said second measurement plate is configured to adjust said enclosed angle ($\alpha$).

15. A surgical instrument according to claim 12, wherein said rotating device is formed by pivoting said second measurement plate along an axle situated perpendicular to the longitudinal axis of said handle and parallel to said first measurement plate.

16. A surgical instrument according to claim 1, wherein said first threaded rod is configured as a tube and said second threaded rod is placed concentrically therein.

17. A surgical instrument according to claim 12, wherein said surgical instrument is manufactured of a biocompatible material.

18. A surgical instrument according to claim 17, wherein said biocompatible material is selected from the group consisting of stainless steel and titanium.

* * * * *